(12) United States Patent
Farri et al.

(10) Patent No.: US 12,183,463 B2
(45) Date of Patent: Dec. 31, 2024

(54) GENERATION OF FINDINGS IN RADIOLOGY REPORTS BY MACHINE LEARNING BASED ON IMPRESSIONS

(71) Applicant: SIEMENS HEALTHINEERS AG, Forchheim (DE)

(72) Inventors: Oladimeji Farri, Upper Saddle River, NJ (US); Ramya Vunikili, Newark, NJ (US)

(73) Assignee: Siemens Healthineers AG, Forchheim (DE)

( * ) Notice: Subject to any disclaimer, the term of this patent is extended or adjusted under 35 U.S.C. 154(b) by 487 days.

(21) Appl. No.: 17/650,896

(22) Filed: Feb. 14, 2022

(65) Prior Publication Data

US 2023/0260649 A1    Aug. 17, 2023

(51) Int. Cl.
*G16H 50/20*     (2018.01)
*G06F 40/40*     (2020.01)
*G06N 3/045*     (2023.01)
*G16H 10/60*     (2018.01)
*G16H 30/20*     (2018.01)

(52) U.S. Cl.
CPC ............. *G16H 50/20* (2018.01); *G06F 40/40* (2020.01); *G06N 3/045* (2023.01); *G16H 10/60* (2018.01); *G16H 30/20* (2018.01)

(58) Field of Classification Search
None
See application file for complete search history.

(56) References Cited

U.S. PATENT DOCUMENTS

| | | | |
|---|---|---|---|
| 2020/0020097 A1* | 1/2020 | Do | G06F 18/2413 |
| 2020/0334809 A1 | 10/2020 | Vianu et al. | |
| 2022/0068449 A1* | 3/2022 | Klassen | G16H 15/00 |
| 2022/0293271 A1* | 9/2022 | Chang | G16H 15/00 |
| 2023/0102428 A1* | 3/2023 | Oktay | G06F 40/30 |
| | | | 382/128 |
| 2023/0207105 A1* | 6/2023 | Wang | G16H 30/40 |
| | | | 382/128 |

OTHER PUBLICATIONS

Devlin, Jacob, et al. "Bert: Pre-training of deep bidirectional transformers for language understanding." arXiv preprint arXiv: 1810.04805 (2018). pp. 1-16.
Dzmitry Bahdanau, Kyunghyun Cho, and Yoshua Bengio. 2015. Neural machine translation by jointly learning to align and translate. The 2015 International Conference on Learning Representations. pp. 1-15.
Eng, J. and Eisner, J.M., 2004. Informatics in radiology (info RAD) radiology report entry with automatic phrase completion driven by language modeling. Radiographics, 24(5), pp. 1493-1501.
(Continued)

*Primary Examiner* — Leon Flores

(57) ABSTRACT

Machine training is used to learn to generate findings in radiology reports. Rather than merely learning to output findings from an input, the machine training uses loss based on impression derived from findings to machine train the model to generate the findings. Once trained, the machine-learned model generates findings but the findings are more accurate or complete due to having used impression loss in the training.

18 Claims, 3 Drawing Sheets

(56) References Cited

OTHER PUBLICATIONS

Hasan, Sadid A., et al. "PRNA at ImageCLEF 2017 Caption Prediction and Concept Detection Tasks." CLEF (Working Notes). 2017. pp. 1-5.
Krause, J., Johnson, J., Krishna, R., & Fei-Fei, L. (2017). A hierarchical approach for generating descriptive image paragraphs. In Proceedings of the IEEE conference on computer vision and pattern recognition (pp. 317-325).
Krishnaraj, Arun, et al. "Voice recognition software: effect on radiology report turnaround time at an academic medical center." American Journal of Roentgenology 195.1 (2010): 194-197.
Luong, Minh-Thang, Hieu Pham, and Christopher D. Manning. "Effective approaches to attention-based neural machine translation." arXiv preprint arXiv:1508.04025 (2015).
Miller, Derek. "Leveraging BERT for extractive text summarization on lectures." arXiv preprint arXiv:1906.04165 (2019). pp. 1-7.
Nallapati, Ramesh, et al. "Abstractive text summarization using sequence-to-sequence rnns and beyond." arXiv preprint arXiv:1602.06023 (2016).
Xue, Yuan, et al. "Multimodal recurrent model with attention for automated radiology report generation." International Conference on Medical Image Computing and Computer-Assisted Intervention. Springer, Cham, 2018. pp. 457-466.
Zhang, Yuhao, et al. "Learning to summarize radiology findings." arXiv preprint arXiv:1809.04698 (2018). pp. 1-10.
Extended European Search Report (EESR) mailed Jul. 3, 2023 in corresponding European Patent Application No. 23156314.9.
Singh, et al; "Show, tell and summarise: learning to generate and summarias radiology findings from medical images"; Neural Computing and application, springere london; vol. 33; No. 13; Date: Apr. 5, 2021; ISSN: 09410643; DOI:10.1007/S00521-021-05943-6.
Anonymous: "deep learning—What dosse end to end training mean?—Artificial Intelligence Stack Exchange" ; Date: Dec. 17, 2021; XP093056893; URL: https://ai.stackexchange.com/questions/16575/what-does-end-to-end-training-mean.
Srinivasan, et al;"Hierarchical X-Ray Report Generation via Pathology Tags and Multi Head Attention"; Date: Dec. 31, 2021; pp. 600-616; XP047578021.

\* cited by examiner

GENERATION OF FINDINGS IN RADIOLOGY REPORTS BY MACHINE LEARNING BASED ON IMPRESSIONS

BACKGROUND

The present embodiments relate to radiology reports. To create a radiology report, a radiologist reviews images and/or data for a patient to determine findings. A conclusion or impression is then formed from the findings. This time-consuming and burdensome process may have undesired variance between radiologists or even by a same radiologist.

Computer-assisted systems assist radiologists. For example, auto-completion of sentences while generating a radiology report is provided. Automated speech recognition may be used to enhance report generation. Other work summarizes radiology reports (i.e., automatic impression generation) from details in the findings section. These systems may save some time, but mostly address either data entry or the less time-consuming generation of an impression from the findings.

SUMMARY

By way of introduction, the preferred embodiments described below include methods, systems, instructions, and non-transitory computer readable media for machine training to generate findings and/or generating a finding in radiology reports by a machine-learned system. Rather than merely learning to output findings from an input, the machine training uses loss based on impression to machine train the model to generate the findings. Once trained, the machine-learned model generates findings but the findings are more accurate or complete due to having used impression loss in the training.

In a first aspect, a method is provided for generating a finding in radiology reports by a machine-learned system. A medical image of a patient is obtained. A first finding is generated by a machine-learned model in response to input of the medical image to the machine-learned model. The machine-learned model trained, at least in part, from training data impressions based on training data findings. The first finding is displayed.

In one embodiment, the first finding is text describing a first occurrence represented in the medical image. The training data findings represent multiple different occurrences (e.g., the first occurrence and a second occurrence), and the training data impressions represent diagnostic conclusions based on the training data findings.

In another embodiment, the machine-learned model is a machine-learned vision model configured to receive the medical image and a machine-learned natural language processing model configured to generate the first finding as text from an output of the machine-learned vision model. For an example, in training this model, the machine-learned model was trained in a sequence where loss from the training data impressions is back propagated to the natural language processing model in a first training and then the vision model and the natural language processing model are trained in a second training.

As another embodiment, the machine-learned model was trained with machine learning by an impression model machine learning to generate output impressions from output findings of the model being trained for the machine-learned model. The training used loss from the training data impressions relative to the output impressions. In a further approach, the machine-learned model was trained where values of learnable parameters of the model being trained for the machine-learned model were changed based on backpropagation from the loss of the training data impressions relative to the output impressions. In another further approach, the machine-learned model was trained where the impression model also received input of patient background information relative to each training data sample, the patient background information encoded with an attentional encoder.

In yet another embodiment, the first finding is generated as a paragraph of patient findings including the first finding. In one example for paragraph generation, the machine-learned model is a machine-learned first neural network configured to detect regions of interest and a machine-learned hierarchal recurrent neural network or a machine-learned bidirectional encoder representations from transformers network configured to generate the first finding from a projection of the detected regions of interest output by the machine-learned first neural network. As a further refinement, the machine-learned hierarchal recurrent neural network is used and is a sentence-level recurrent neural network outputting to a word-level recurrent neural network.

In other embodiments, the first finding is integrated into a radiology report including a first impression created by a physician, and the radiology report is displayed. Alternatively, or additionally, a comparison of the first finding with a physician created finding is displayed.

In a second aspect, a method is provided for machine training to generate findings. A first model is defined to receive images and output findings. A second model is defined to receive finding and output impressions. The first model is machine trained, at least in part, based on losses from the output impressions compared to ground truth impressions. The machine-trained first model is stored.

In one embodiment, the first model is defined as a vision model configured to receive the images and a natural language processing model configured to output the findings as text from an output of the vision model. In a further embodiment, training is done in a sequence where the loss from the output impressions compared to the ground truth impressions is back propagated to the natural language processing model in a first training and then the vision model and the natural language processing model are trained in a second training.

In another embodiment, the machine training includes training where values of learnable parameters of the first model are changed based on backpropagation from the losses.

As another embodiment, the machine training includes machine training the second model based on the losses where the second model also receives input of patient background information relative to each training data sample, the patient background information encoded with an attentional encoder.

In yet another embodiment, the first model is defined as a first neural network configured to detect regions of interest and a hierarchal recurrent neural network or a bidirectional encoder representations from transformers network configured to generate the findings from a projection of the detected regions of interest output by the first neural network. In a further embodiment, the first model is defined as the hierarchal recurrent neural network. The hierarchal recurrent neural network is a sentence-level recurrent neural network outputting to a word-level recurrent neural network.

In a third aspect, a system is provided for creating an anatomical observation. A medical records database stores an image of and/or text describing a patient. A processor is configured to input the image and/or text to a machine-trained model configured to create a first anatomical observation in response to input of the image and/or the text. The machine-trained model was trained with a loss based on diagnostic conclusion derived from second anatomical observations. A display is configured to output the first anatomical observation for the patient.

The present invention is defined by the following claims, and nothing in this section should be taken as a limitation on those claims. Any embodiments or aspects in one type of claim (e.g., method, system, or non-transitory computer readable media) may be provided in another type of claim. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views. The PHI in the drawings is made up for illustration purposes and does not represent an actual patient.

DETAILED DESCRIPTION OF THE DRAWINGS AND PRESENTLY PREFERRED EMBODIMENTS

Auto-generation of medical image and/or text findings in radiology reports uses machine training of artificial intelligence (AI) from impressions. An ensemble of vision and text algorithms generates findings directly from medical images and/or text. Based on training using impressions from findings, the impressions intermediately support the model training for findings. This approach reverses natural language generation, i.e., generating findings from impression, to learn to generate findings using loss from impression.

The trained AI generates findings, taking over the burden of documenting detailed descriptions of the findings. By putting together computer vision and natural language processing (NLP) algorithms, radiologists can document their impressions, while the machine generates the corresponding findings. Radiologists focus their cognitive efforts on reasoning and documenting accurate and actionable conclusions (impressions) after reviewing medical images, while the AI system, such as natural language processing (NLP) and computer vision models, automatically generates the descriptions of the imaging findings. In this paradigm, the AI system takes over the burden of documenting detailed descriptions of the findings, thereby making the radiologist more efficient and less encumbered with administrative (albeit important) tasks. The resulting gain in worktime may be allocated to interacting or reasoning with other clinicians managing the patient, thereby giving radiologists the chance to be more actively involved in patient care. Overall, the AI system affords radiologists the opportunity to emphasize their role as clinicians actively involved in the multi-disciplinary approach to patient care, rather than current assumptions that limit their role to "image reading."

Less experienced radiologists may use the AI as a baseline to evaluate if they can identify the important findings that informed the impressions in reports from more experienced radiologists, facilitating improved clinical education. The machine-generated findings are utilized in evaluating the radiologist-derived findings to identify discrepancies and potential areas for training/competence improvement.

Figure 1:
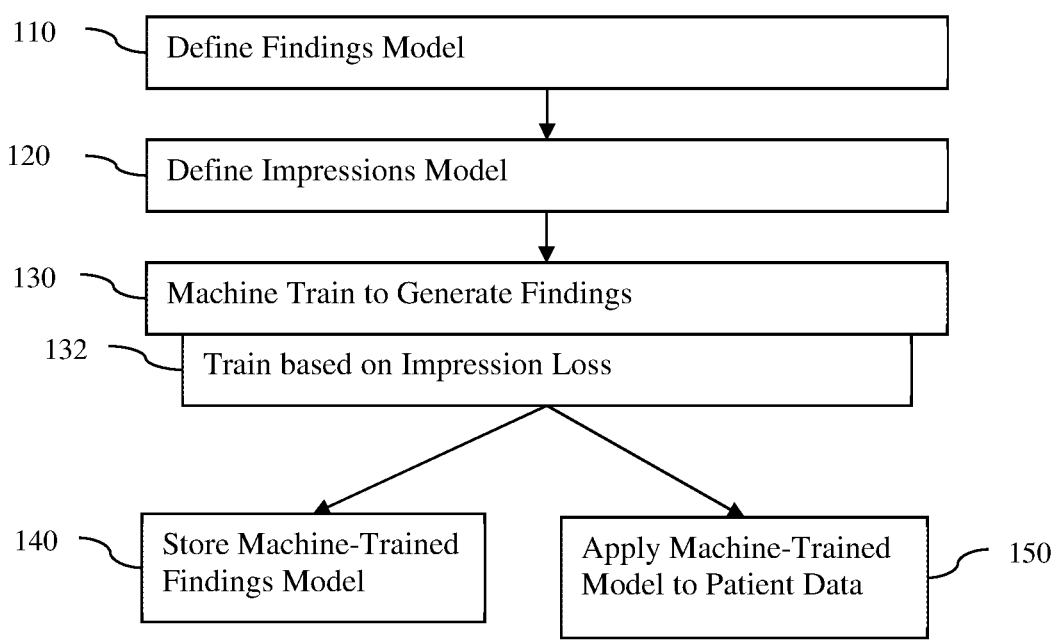
FIG. 1 is a flow chart diagram of an embodiment of a method for machine training using loss from impressions to generate findings.

FIG. 1 shows one embodiment of a method for machine training to generate findings. A model is machine trained to generate findings where the training includes loss from impressions created from the findings, allowing the impressions to inform the values of the learnable parameters for the model trained to generate findings. How the model is trained results in the trained model being different. By using impression as an intermediary through training, the resulting trained model to generate findings is configured and operates to provide more accurate or complete findings.

Figure 2:
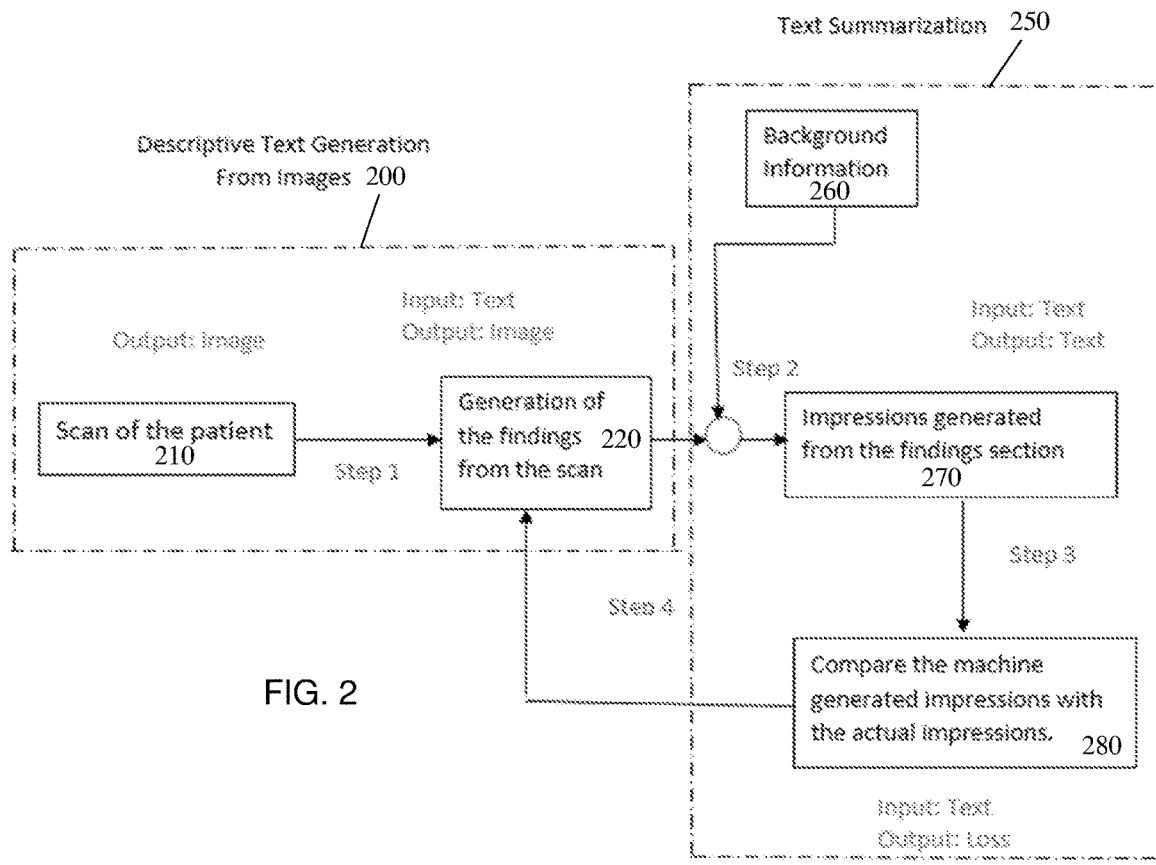
FIG. 2 shows an example arrangement of training to generate findings using loss based on impressions.

The proposed training solution contains two parts: descriptive text generation (i.e., findings) from images and text summarization (i.e., impression generation from findings). FIG. 2 shows an example arrangement for training.

Figure 5:
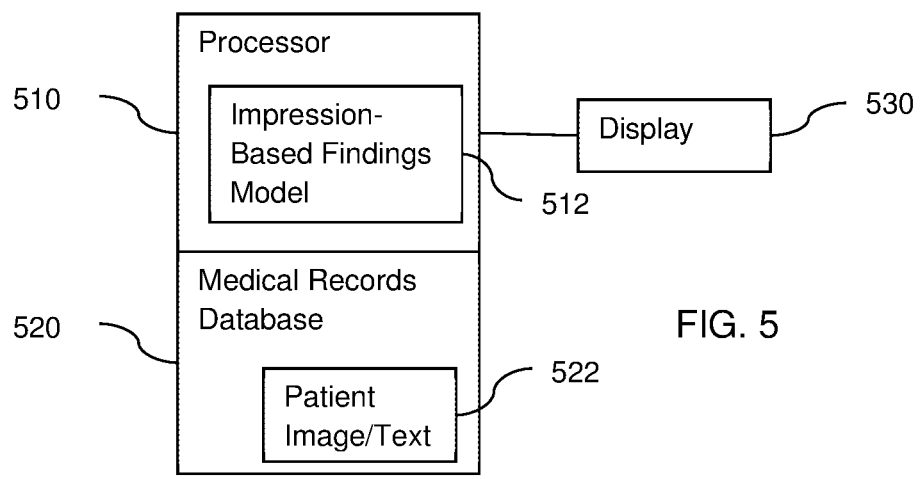
FIG. 5 is a block diagram of one embodiment of a system for findings generation based on impression training.

The method of FIG. 1 is implemented by the system of FIG. 5 or another system. For example, the method is implemented by a computer, server, or other processor. The implementation of the method uses the arrangement of FIG. 2 or a different arrangement.

Additional, different, or fewer acts may be provided. For example, act 140 and/or act 150 are not performed. As another example, acts 110 and 120 are combined to define both the findings and impression models together. Acts for gathering training data may be provided.

The acts are performed in the order shown (e.g., top to bottom or numerical) or other orders. For example, act 120 may be performed prior to act 110. As another example, act 132 is performed as part of act 130 or in sequence with act 130. Act 150 may be performed before, after, or at a same time as act 140.

In act 110, the findings model is defined. The architecture of the model to be trained to output findings is defined. The model, including layers, nodes, activation functions, processes, connections, and learnable parameters is defined in a computer. The defined model is stored in a memory or loaded into the processor for machine training.

The findings model is configured to output findings, in part, by the definition. This task of outputting findings is comparable to generation of descriptive paragraphs for an image. The findings are factual statements about anatomy or other characteristic represented in the image or text. For example, in a chest x-ray, the findings include "no costophrenic angle" and "fluid located in a right lung base." The impression is the summary or diagnostic conclusion from the findings, such as "the patient suffering from a bilateral plural effusion in the right lung."

The findings model is a model for machine learning. The model is the architecture including learnable parameters that is to be trained by the machine. The findings model is defined or configured to receive one or more images and/or text and output one or more findings. FIG. 2 shows the finding model 220 as part of descriptive text generation from images 200. The image output by the scan 210 is to be input to the findings model 220 in step 1 for generation of the findings from the scan. In training, many samples of images from many patients are provided. The samples may include findings, images, text, background information, and/or impressions, such as the samples being radiology reports with images, findings, and impressions.

The findings model 220 is a neural network, support vector machine, transformer network, combination thereof, or another model for machine learning. In one embodiment, the findings model 220 includes a vision model configured to receive the images and a NLP model configured to output the findings as text generated from an output of the vision model. For example, the vision model portion of the findings model 220 is an encoder-decoder framework (e.g., generative model) formed from a neural network, such as an encoder-decoder framework that is a VGGnet-9 or another convolutional neural network (CNN) model fine-tuned on medical images as the vision model. As another example, the NLP portion of the findings model 220 is a long-short-term memory (LSTM) model with an attention mechanism.

In another embodiment, the findings model 220 includes a neural network with any number of layers configured to detect characteristics represented in the image as the vision model. The image is input to the neural network. Other types of neural networks (e.g., fully connected network) may be used, and/or other characteristics (e.g., landmarks) may be detected for the vision model of the findings model.

The NLP model receives outputs, such as features or output characteristics, from the vision model and generates text, such as words, bullet points, sentences, paragraphs, captions, annotations, and/or another format for findings. The NPL model is a neural network, such as a hierarchal recurrent neural network or a bidirectional encoder representations from transformers (BERT) network.

Figure 3:
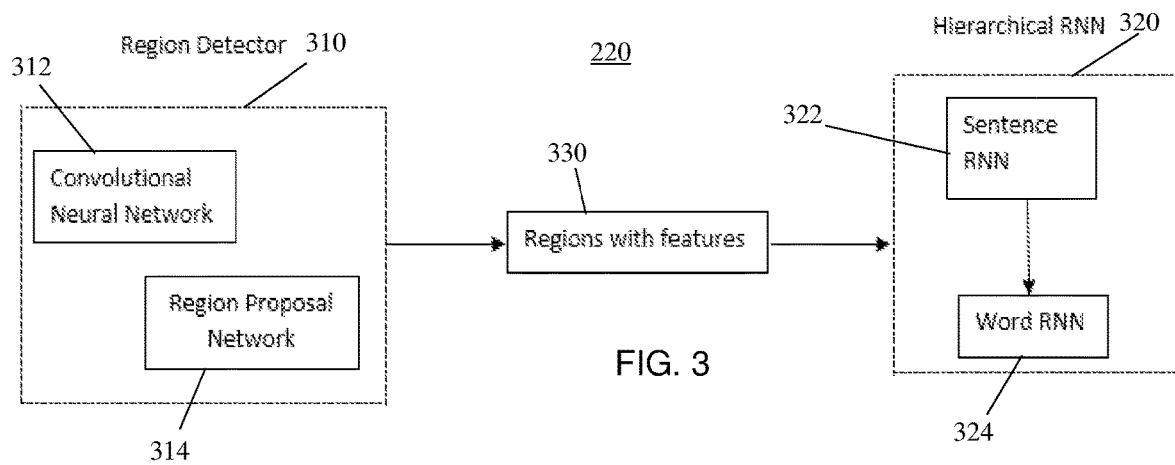
FIG. 3 illustrates an example machine-learned findings generation model.

FIG. 3 shows an example of the findings model 220 where the vision model is a region detector 310. A convolutional neural network (CNN) 312 is used to detect regions as the characteristic in the region detector 310. The CNN 312 generates feature maps input to the region proposal network 314, which is a classifier or generator for identifying regions of interest. The regions or a projection from the regions (e.g., derived feature values) 330 are output from the vision model for input to the NLP model. In the example of FIG. 3, the NLP model is a hierarchal recurrent neural network 320 configured to generate the findings from a projection of the detected regions of interest 330 output by the vision model (e.g., CNN 312 and/or region proposal network 314).

The task of generating findings from the image can be done by generating multiple sentence-level findings or a single paragraph. Generating a paragraph or paragraphs for the findings may be a better alternative as the sentence-level findings may be redundant. FIG. 3 shows one embodiment of the findings model 220 to obtain paragraph-level findings. The region detector 310 proposes different regions of interest (ROI) in a given image, which regions are then projected to a convolutional feature map by the CNN 312. The aggregated output from the region detector can be used to describe the image in a compact way as regions 330 with features. This image representation is fed to the hierarchical recurrent network 320. The hierarchy is a sentence-level recurrent neural network (RNN) 322 and a word-level RNN 324. The sentence-level RNN 322 determines the number of sentences that need to be generated along with sentence topic vectors. These sentence topic vectors are then consumed by word-level RNN 324 to generate the sentences in a paragraph form as one or more findings.

In alternative embodiments, the findings model is a multimodal recurrent model with attention for automated report generation. An image encoder of the multimodal recurrent model is the vision model, and sentence and recurrent paragraph generative models are the NLP model. In another alternative, a BERT-based model is used as the NLP model.

Referring again to FIGS. 1 and 2, an impressions model is defined in act 120. The architecture of the model to be trained to output impressions is defined. The impression model, including layers, nodes, activation functions, processes, connections, and learnable parameters is defined in a computer. The defined model is stored in a memory or loaded into the processor for machine training.

The impression model is configured to output impressions based on input of findings. The impression model has a different architecture than the findings model but may include the same or similar arrangements. In FIG. 2, the impressions model 270 receives the findings output by the findings model 220 in step 2. The impression model 270 condenses the findings to a shorter summary (impression) using a text summarization model. The text summarization model may be BERT-based architecture with topic-aware attention mechanism and reinforcement learning. In other embodiments, the impression model 270 is a neural network with LSTM or another NLP model.

The impression model 270 may be configured to operate on other inputs in addition to the findings. In the example of FIG. 2, background information 260 is input to provide context. The impression model 270 is configured to include inputs for the findings and inputs for the background information. The input for the background information may include or be an attentional encoder. Over sequence-to-sequence and pointer generator networks may be used.

In training, the background information for each training sample is provided. In order to give more context to the text summarization model, findings are combined with the background information 260 (metadata) of the images 210 including the clinical diagnosis or indication related to the imaging procedure, anatomical structures involved, and/or clinical history (e.g., test results, patient history, and/or presenting symptoms) of the patient. The metadata is encoded using a separate attentional encoder and the resulting representation is used in guiding the decoding process of generating an impression from findings.

In act 130, a machine trains the defined findings and impression models 220, 270. The machine training uses a machine training algorithm for the defined architecture. The finding model is machine trained, at least in part, based on losses from the output impressions of the impression model. The impression loss is between the model output impressions and the ground truth impressions, such as provided in the training data (e.g., from radiology reports of past patients). The machine-generated impressions are compared to the impressions written by the radiologists (ground truth) to iteratively compute a loss function. The loss function provides a way to optimize the findings model and impression model depending on how different the two impressions are from each other.

A processor performs machine learning to create a machine-trained model to generate findings. For training, the training data includes many samples. The samples are the images, text, background information, and/or other information to be used as inputs to the findings and impression models. For example, the training data are radiology reports with labeled sections identifying the impressions, findings, and images. The samples include medical report text and/or images as input for the findings model. The samples also include the ground truth, such as ground truth findings and/or ground truth impressions, for supervised learning.

The impressions model 270 is an intermediary used in training the findings model 220. The impression losses inform the learning of the values of the learnable parameters of the findings model 220. Findings losses may be used as well, such as with a joint loss as a weighted sum of the findings loss and impression loss or such as with sequential training of the findings model 220 using the findings loss and then the impression loss, or vise versa. Once trained, the findings model 220 is or may be used without the impressions model 270.

Referring to FIG. 2, the comparison 280 of step 3 receives the impressions output by the impression model during training of the impression model 270 and findings model 220. The comparison 280 of the machine generated impressions with the actual or ground truth impressions forms a loss, such as a mathematical encoding of differences between matrices formed with the impressions. Given the impressions generated by the impressions model 270, the difference between the ground truth impressions and those generated by the machine are mathematically modeled to give a loss function for the ensemble.

In machine training, the values of learnable parameters of the finding model are optimized to minimize the impression loss. The many samples of training data are used in the optimization. In step 4, the loss is fed back to at least the findings model 220 as back propagation to adjust or change the values of the learnable parameters of the findings model 220. The impression model 270 may have been previously trained or may also receive the back propagation of the loss to alter one or more values of learnable parameters. Any optimization may be used to alter the values based on the losses, such as gradient descent or Adam.

In one embodiment, the machine learning varies over time. A sequence of different learning approaches is used. The training is performed in a sequence. In one part of the sequence, the loss from the output impressions of the impression model 270 compared 280 to the ground truth impressions is back propagated to the NLP model 320, the vision model, and/or the findings model 220 in a first training. In a second part, the vision model, NLP model, and/or the findings model are then trained using findings loss in a second training. As another example, the loss calculated in step 3 of FIG. 2 is backpropagated into the hierarchical RNN network forming the impressions model so that the impressions model can be penalized for any difference between the actual impressions and the machine-generated impressions based on the machine generated findings. As the hierarchical RNN model of the impression model becomes more accurate with accurate impressions from training samples of findings, then a CNN+RNN model (findings model 220 or both vision and NLP models) is trained on images with loss back propagated from impressions, such that the findings model can take a medical image as input and generate the findings as the output while leveraging the loss function of the hierarchical RNN forming the impressions model. The training data findings may be used for a joint loss or sequentially in training the findings model.

In act 140 of FIG. 1, the processor stores the machine-trained findings model. The machine-trained impression model may also be stored, such as where both findings and impression models are to be applied. Where the impression model is used without the impression model, the findings model is stored. Since the impressions loss was used in training the findings model, the values of the learned parameters of the findings model were influenced by the impressions loss so that the findings are more accurate or complete.

The trained model is stored in a memory. The trained AI is stored. The result of the training is a matrix or other model representation.

Any memory may be used. The memory used for the traning data may be used. For application, the memory may be in other devices. For example, the trained model is stored in a memory of a server. The server uses the trained model to output to clients. As another example, multiple copies of the trained model are provided to different users and/or workstations for use by different users.

In act 150, the processor used for training or a different processor applies the machine-trained model to images and/or text for a given patient. This patient data (e.g., image) is previously unseen by the machine-trained model (i.e., different image than used to train). Once trained, the machine-learnt model is applied by a machine, such as a computer, processor, or server. The machine uses input data for a patient (e.g., image and/or text) and the machine-learned findings model to generate one or more findings.

Figure 4:
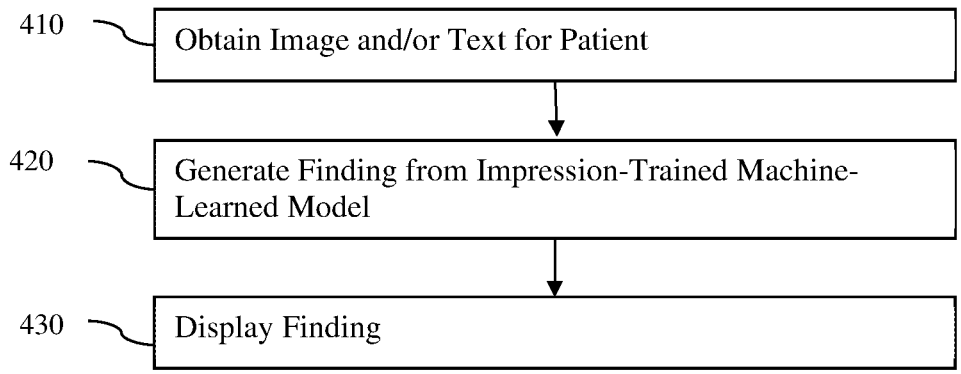
FIG. 4 is a flow chart diagram of one embodiment of a method for generating findings with a machine-learned model having been trained based on impressions.

FIG. 4 is a flow chart diagram of one embodiment of a method for generating a finding in radiology reports by a machine-learned system. FIG. 4 is an example application of, test phase for, or inference by the machine-learned findings model. The findings model resulting from training using impression loss is applied to data for a patient.

The method is implemented by the system of FIG. 5 or another system. For example, the processor, using access to a memory or computer network interface, obtains an image for a patient. As another example, a medical imager or scanner obtains the image. The processor generates the findings by applying an impression-trained machine-learned model to the image. The processor, using a display, displays the finding.

The method is performed in the order shown (numerical or top to bottom) or other order. Additional, different, or fewer acts may be included. For example, acts for machine generating an impression and displaying the impression are added. As another example, the findings are added to a computerized medical record and stored instead or in addition to display.

In act 410, a processor obtains a medical image of a patient. The image is obtained by scanning the patient, such as with an x-ray, computed tomography, magnetic resonance, positron emission tomography, single photon emission computed tomography, ultrasound, or another medical imaging. In other embodiments, the image is obtained by loading from memory, such as accessing a DICOM file for the image, or by receipt from computer network.

The image may be obtained from a template of a radiology report. For example, a previously or just created image is added to a report being generated. The image is obtained from that report.

In addition, or as an alternative, text is obtained. Text for clinical information or other sources of text related to the patient may be obtained. The machine-learned model may have been trained to receive one or more images, text, and/or both as input to generate the findings.

In act 420, the processor generates one or more findings. A machine-learned model generates the findings in response to input of the medical image and/or text to the machine-learned model. Once a patient undergoes an imaging procedure, the image generated is fed as an input to the computer vision and NLP models to generate a caption or other findings for the image. The findings are generated as text describing one or more occurrences represented in the medical image. For example, the anatomy or another object represented in the image is described as the finding. The text for the findings may be one or more bullet points, sentences, and/or paragraphs representing the findings.

The machine-learned model was previously trained. During application for this patient and/or other patients, the values of the learnable parameters are not changed. In this "inference" phase, the previously trained model is applied to previously unseen inputs.

The output finding depends on the values of the learnable parameters. Thus, the training to optimize those values directly affects the findings output in application. The way or how the machine-learned model was trained results in a given output when the trained model is applied.

The machine-learned model was trained, at least in part, from training data impressions based on training data findings. For example, findings for one, two, or more different occurrences in sample images are used in training. Impressions from those findings and/or image are used as ground truth. The training data impressions represented diagnostic conclusions based on the training data findings. The values of the learnable parameters for the machine-learned model generating the findings are based (e.g., changed in optimization), at least in part, on backpropagation of a loss using the impressions formed from the findings. The loss is from the training data impressions relative to the output impressions. For example, the training arrangement of FIG. 2 is used where an impression model is machine trained to output machine impressions from machine findings output by the findings model. The impressions model is trained jointly with or in sequence with the findings model. The impression model may receive other inputs in the training, such as background information for the patient providing context.

In one embodiment, the machine-learned model for generating the finding or findings includes a machine-learned vision model configured to receive the medical image and a machine-learned NLP model configured to generate the finding or findings as text from an output of the machine-learned vision model. In this embodiment, the loss from the impressions may have been back propagated to the vision model, NLP model, or both in training. In one embodiment, the machine-learned model was trained in a sequence where loss from the training data impressions is back propagated to the NLP model or the impressions model in a first training and then the vision model and the NLP model of the findings model are trained in a second training using backpropagation of the loss from impressions.

In one embodiment, the machine-learned model for generating findings is a machine-learned neural network configured to detect regions of interest and a machine-learned hierarchal recurrent neural network or a machine-learned bidirectional encoder representations from transformers network configured to generate the findings from a projection of the detected regions of interest output by the machine-learned neural network. In an example, the machine-learned hierarchal recurrent neural network is used. The hierarchal recurrent neural network includes a sentence-level recurrent neural network outputting to a word-level recurrent neural network, which outputs the findings. Other arrangements may be used.

In act 430, one or more findings are displayed. The display is on a display screen, such as a display for a computer, workstation, or terminal. In other embodiments, the display is on paper by printing.

In one embodiment, the findings are displayed as part of a user interface for a radiologist. For example, a list of findings is presented with the input image and/or text so that the radiologist may confirm the findings and/or create an impression from the findings. In another embodiment, the findings are integrating into a radiology report. The findings may be included in the radiology report as part of creating the report and/or included with one or more impression created by the radiologist. The radiology report as completed and/or while being created is displayed to output the findings.

In another embodiment, the display is of the machine-generated findings for comparison with radiologist or physician created findings. The findings may be displayed side-by-side for comparison. The image may be displayed so that the radiologist can verify accuracy of their or the machine-generated findings.

FIG. 5 is a block diagram of one embodiment of a system for creating an anatomical observation as a finding. Any finding may be created by the system. For example, the system implements the method of FIG. 4. In alternative embodiments, the system of FIG. 5 is used in training so implements the method of FIG. 1 and/or the arrangement of FIG. 2.

The system includes one or more medical records databases 520 with one or more patient images and/or text 522, a processor 510 for applying an impression-based findings model 512, and a display 530. Additional, different, or fewer components may be provided. For example, a network or network connection or interface is provided, such as for networking with a medical imaging network or data archival system or interconnecting the processor 510 and the database 520. In another example, additional processors 126, databases 520, and/or machine-learned models (e.g., impression model) are provided.

The medical records database 520, processor 510, and/or display 530 are part of a medical imager, server, workstation, or computer. In one embodiment, the medical records database 520, processor 510, and/or display 530 are part of a personal computer, such as desktop or laptop. In yet other embodiments, the medical records database 520 is part of a separate computer from the processor 510, such as being a picture archiving and communications system (PACS).

The medical records database 520 is a random access memory, system memory, cache memory, hard drive, optical media, magnetic media, flash drive, buffer, database, combinations thereof, or other now known or later developed non-transitory memory device for storing the patient image and/or text 522 describing the patient, the impression-based findings model 512, findings, impressions, radiology report, and/or data generated by, during, or for application of the impression-based findings model 512. The medical records database 520 is part of the computer associated with the processor 510 or is a separate or remote database for access over a computer network. More than one database 520 may be provided, such as separate databases for different practice groups and/or locations in a same medical institution. The database or databases 520 store one or more patient files, such as being part of a computerized patient medical record system.

The medical records database 520 or other memory is alternatively or additionally a non-transitory computer readable storage medium storing data representing instructions executable by the programmed processor 510. The instructions for implementing the creation of findings from input image or text 522 are stored. The instructions for implementing the processes, methods, and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code, and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 510 is a general processor, control processor, digital signal processor, application specific integrated circuit, field programmable gate array, tensor processing unit, graphics processing unit, AI processor, or other hardware processor for application of a machine-learned model, such as the impression-based findings model 512. The processor 510 is part of a computer, workstation, server, or other device configured to apply machine learning and/or to apply a machine-learned model. The processor 510 is configured by software, hardware, and/or firmware. For learning, the processor 510 is configured by one or more machine learning algorithms. For applying a learned model, the processor 510 is configured, in part, by a learned matrix or matrices, table, architecture with values for learned parameters, or another model representation associating input data to output data.

The processor 510 is configured to input the image and/or text to a machine-trained model. The machine-trained model is configured to create one or more anatomical observations or other types of findings in response to input of the image and/or the text 522. The machine-trained model was trained with a loss based on diagnostic conclusion (impression) derived from anatomical observations, so is the impression-based findings model 512. The processor 510 may be configured for re-training using training data gathered through application and any corrections made by radiologists.

The display 530 is a monitor, LCD, projector, plasma display, CRT, printer, or another now known or later developed device for displaying findings (e.g., anatomical observation or observations for the patient) with or without the input text, input image, background information, and/or impressions. The display 530 may display a radiology report being created or as created.

The processor 510 formats the data into an image and stores the image in a buffer, configuring the display 530. The display 530 uses the image in the buffer to generate an image for viewing. The image includes graphics, alphanumeric text, image, and/or other information.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for generating a finding in radiology reports by a machine-learned system, the method comprising: obtaining a medical image of a patient; generating a first finding by a machine-learned model in response to input of the medical image to the machine-learned model, the machine-learned model trained, at least in part, from training data impressions based on training data findings, wherein the machine-learned model comprises a machine-learned first neural network configured to detect regions of interest and a machine-learned hierarchal recurrent neural network or a machine-learned bidirectional encoder representations from transformers network configured to generate the first finding from a projection of the detected regions of interest output by the machine-learned first neural network; and displaying the first finding.

2. The method of claim 1 wherein generating the first finding comprises generating text describing a first occurrence represented in the medical image, where the training data findings represented the first and a second occurrence and the training data impressions represented diagnostic conclusions based on the training data findings.

3. The method of claim 1 wherein generating comprises generating by the machine-learned first neural network comprising a machine-learned vision model configured to receive the medical image, and the first finding comprising text generated from an output of the machine-learned vision model.

4. The method of claim 3 wherein the machine-learned model was trained in a sequence where loss from the training data impressions is back propagated to an impressions model in a first training and then the vision model and the machine-learned hierarchal recurrent neural network or the machine-learned bidirectional encoder representations from transformers network are trained in a second training.

5. The method of claim 1 wherein generating comprises generating by the machine-learned model having been trained with machine learning by an impression model machine learning to generate output impressions from output findings of the model being trained for the machine-learned model, the training having used loss from the training data impressions relative to the output impressions.

6. The method of claim 5 wherein the machine-learned model was trained where values of learnable parameters of the model being trained for the machine-learned model were changed based on backpropagation from the loss of the training data impressions relative to the output impressions.

7. The method of claim 5 wherein the machine-learned model was trained where the impression model also received input of patient background information relative to each training data sample, the patient background information encoded with an attentional encoder.

8. The method of claim 1 wherein generating the first finding comprises generating the first finding as a paragraph of patient findings including the first finding.

9. The method of claim 1 wherein the machine-learned hierarchal recurrent neural network is used and comprises a sentence-level recurrent neural network outputting to a word-level recurrent neural network.

10. The method of claim 1 wherein displaying comprises integrating the first finding into a radiology report including a first impression created by a physician and displaying the radiology report.

11. The method of claim 1 wherein displaying comprises displaying a comparison of the first finding with a physician created finding.

12. A method for machine training to generate findings, the method comprising: defining a first model to receive images and output findings, wherein the first model is defined as a first neural network configured to detect regions of interest and a hierarchal recurrent neural network or a bidirectional encoder representations from transformers network configured to generate the findings from a projection of the detected regions of interest output by the first neural network; defining a second model to receive findings and output impressions; machine training the first model, at least in part, based on losses from the output impressions compared to ground truth impressions; and storing the machine-trained first model.

13. The method of claim 12 wherein defining the first model comprises defining the first model as a vision model configured to receive the images and a natural language processing model configured to output the findings as text from an output of the vision model.

14. The method of claim 13 wherein machine training comprises training in a sequence where the loss from the output impressions compared to the ground truth impressions is back propagated to the second model in a first training and then the vision model and the natural language processing model are trained in a second training.

15. The method of claim 13 wherein defining the first model comprises defining the first model as the hierarchal recurrent neural network, the hierarchal recurrent neural network comprising a sentence-level recurrent neural network outputting to a word-level recurrent neural network.

16. The method of claim 12 wherein machine training comprises training where values of learnable parameters of the first model are changed based on backpropagation from the losses.

17. The method of claim 12 wherein machine training comprises machine training the second model based on the losses where the second model also receives input of patient background information relative to each training data sample, the patient background information encoded with an attentional encoder.

18. A system for creating an anatomical observation, the system comprising: a medical records database having stored therein an image of a patient; a processor configured to input the image to a machine-trained model configured to create a first anatomical observation in response to input of the image, the machine-trained model having been trained with a loss based on diagnostic conclusion derived from second anatomical observations, wherein the machine-trained model comprises a machine-trained first neural network configured to detect regions of interest and a machine-trained hierarchal recurrent neural network or a machine-trained bidirectional encoder representations from transformers network configured to generate the first anatomical observation from a projection of the detected regions of interest output by the machine-learned first neural network; and a display configured to output the first anatomical observation for the patient.

* * * * *